United States Patent
Ferrari

(10) Patent No.: US 9,149,514 B2
(45) Date of Patent: *Oct. 6, 2015

(54) COMPOSITION AND METHOD FOR TREATING PAPILLOMA VIRUS AND EQUINE SARCOIDS

(75) Inventor: Stefano Ferrari, Rhinebeck, NY (US)

(73) Assignee: MURAMI PHARMA, INC, Rhinebeck, NY (US)

(*) Notice: Subject to any disclaimer, the term of this patent is extended or adjusted under 35 U.S.C. 154(b) by 597 days.

This patent is subject to a terminal disclaimer.

(21) Appl. No.: 12/905,135

(22) Filed: Oct. 15, 2010

(65) Prior Publication Data

US 2011/0027255 A1    Feb. 3, 2011

Related U.S. Application Data

(62) Division of application No. 12/039,948, filed on Feb. 29, 2008, now Pat. No. 7,846,430.

(60) Provisional application No. 60/892,573, filed on Mar. 2, 2007.

(51) Int. Cl.
*A61K 38/47* (2006.01)

(52) U.S. Cl.
CPC ..................... *A61K 38/47* (2013.01)

(58) Field of Classification Search
None
See application file for complete search history.

(56) References Cited

U.S. PATENT DOCUMENTS

| 5,019,411 | A | 5/1991 | Johnson et al. |
| 5,200,182 | A * | 4/1993 | Kiczka .......................... 424/94.5 |
| 6,147,086 | A | 11/2000 | Brenman |
| 2005/0008631 | A1 | 1/2005 | Lee-Huang et al. |

OTHER PUBLICATIONS

Huang, H., Huang, S.-Y., Chen, T.-T., Chen, J.-C., Chiou, C.-L., and Huang, T.-M., "Cisplatin Restores p53 Function and Enhances the Radiosensitivity in HPV16 E6 Containing SiHa Cells", Journal of Cellular Biochemistry 2004, vol. 91, pp. 756-765.*
Hannemann, J., Wunderle, W., and Baumann, K., "Nephrotoxicity of acyclovir and cis-diamminedichloroplatinum(II)—effect of co-administration in rats", Journal of Cancer Research and Clinical Oncology 1992, vol. 118, pp. 181-186.*
Newton, D.L., Kaur, G., Rhim, J.S., Sausville, E.A., and Rybak, S.M. "RNA Damage and Inhibition of Neoplastic Endothelial Cell Growth: Effects of Human and Amphibian Ribonucleases", Radiation Research 2001, vol. 155, pp. 171-174.*
Altamar-Rios, J. "Lysozyme in the treatment of juvenile laryngeal papillomatosis. A new concept in its etiopathogenesis", Anales Otorrinolaringologicos Iber-americanos 1990, vol. 17, pp. 495-504. English translation.*
Yuan, et al; Journal of Virology, (Jul. 2008), vol. 82, No. 13, pp. 6481-6491.
CDC Fact Sheet "Genital HPV" Dec. 2007 (2 pages), retrieved from URL: <http://www.cdc.gov/STD/HPV/STDFact-HPV.htm> on Nov. 18, 2009.
deVilliers et al, "Classification of papillomaviruses" Virology, 2004, vol. 324, pp. 17-27.
Schiffman et al, "Human Papillomavirus: Epidemiology and Public Health", Arch Pathol Lab Med, 2003, vol. 127, pp. 930-934.

* cited by examiner

*Primary Examiner* — Allison Fox
*Assistant Examiner* — Michelle F Paguio Frising
(74) *Attorney, Agent, or Firm* — Norris McLaughlin & Marcus, P.A.

(57) ABSTRACT

A composition of lysozyme and a pharmaceutically acceptable carrier is active against the papilloma virus in both humans and animals. The composition can be used to treat women suffering from cervical cancer. The composition can also be used to treat cows and horses suffering sarcoids.

15 Claims, No Drawings

COMPOSITION AND METHOD FOR TREATING PAPILLOMA VIRUS AND EQUINE SARCOIDS

This application is a Divisional of U.S. application Ser. No. 12/039,948, filed Feb. 29, 2008, now allowed, which claims priority benefit under 35 U.S.C. §119(e) of U.S. Provisional Application No. 60/892,573 filed Mar. 2, 2007.

BACKGROUND OF THE INVENTION

1. Field of the Invention

The present invention relates generally to compositions useful for treating certain viral infections and pathological disorders caused thereby.

2. Description of Related Art

Papilloma virus, a sexually transmitted disease in human, is, among other things, the primary cause of cervical cancer. Current treatments for papilloma virus in humans depend on the type of papilloma virus involved. Thus, more than 100 different types of human papilloma virus exist. Recently a human vaccine has been introduced in the marketplace in order to protect against the strains that cause cervical cancer. In other mammals, such as bovine and equine species, papilloma virus (i.e. bovine and equine papilloma virus) constitutes a serious disease that produces large skin tumors, known as sarcoids. Currently, there is no effective permanent treatment for bovine or equine papilloma virus or sarcoids. Current therapies span from home made concoctions to chemotherapy to surgery. Seldom do any of these therapies prove successful, especially in the long run. Moreover, the use of chemotherapeutic drugs and surgery is very expensive. Accordingly, there remains a need in the art for new and effective treatments against papilloma virus infections in humans and animals, and against sarcoids.

Lysozyme is a known antiviral, which has shown strong action against gram-positive pathogens, such as the herpes virus in human and animal models. However, the action of lysozyme against papilloma virus, in particular, has not heretofore been described.

BRIEF SUMMARY OF THE INVENTION

It has surprisingly been discovered that lysozyme is effective in treating papilloma virus infections in humans and animals, and in treating sarcoids.

Accordingly, the present invention relates in a first embodiment to a composition for treating a papilloma virus infection in a mammal, wherein the composition comprises an antivirally effective amount of a lysozyme and a pharmaceutically acceptable carrier.

The present invention relates in a second embodiment to a method of treating a papilloma virus infection in a patient in need thereof by administering the inventive composition to the patient in an effective amount and for a period of time sufficient to treat the papilloma virus infection.

The present invention relates in a third embodiment to a method of treating sarcoids in a bovine or equine animal suffering therefrom comprising administering to the animal or topically applying to the sarcoids the inventive composition in an effective amount and for a period of time sufficient to treat the sarcoids.

DETAILED DESCRIPTION OF THE INVENTION

The inventive composition comprises a content of a lysozyme. The lysozyme can be naturally-occurring, synthetic or recombinant. In principal, all lysozymes are useful in the inventive composition, although the intended use of the inventive composition may suggest to those skilled in the art a preference for one type of lysozyme as opposed to another. In one preferred embodiment, the lysozyme is a human recombinant lysozyme, for example, as is disclosed in U.S. Pat. No. 6,991,824, the entire contents of which are hereby incorporated herein by reference. In another preferred embodiment, the lysozyme is a non-human lysozyme, especially a hen egg white lysozyme.

In a preferred embodiment, the inventive composition additionally comprises at least one additional therapeutic agent effective against papilloma virus. These additional therapeutic agents can be chemotherapeutic agents or other antiviral compounds. The lytic activity of lysozyme on the virus envelop can be expected to improve the effectiveness of such additional therapeutic agents.

Thus, the inventive composition can further comprise an effective amount of one or more antiviral agents, antiseptic agents, chemotherapeutic agents, immunopotentiating agents, or mixtures thereof. Preferably, the additional therapeutic agent is selected from the group consisting of acyclovir, vidarabine, uridine, 5-fluorouracil, thiotepa, interferons, podophyllotoxin, trichloroacetic acid, salicylic acid, carbamide peroxide, hexamethylene tetramine, cisplatin, and derivatives of each of the foregoing therapeutic agents. In one especially preferred embodiment, the additional therapeutic agent is acyclovir. In another especially preferred embodiment, the additional therapeutic agent is cisplatin. Generally, it has been shown that acyclovir and the other compounds mentioned are effective in reducing abnormal skin growth conditions [*Atlas, Microbiology, Fundamentals and Applications*, p 551, MacMillan, New York, London, (1984)]. In addition, 5-fluorouracil and thiotepa exhibit significant antineoplastic activities. The usage of podophyllotoxin, trichloroacetic acid, and salicylic acid is also documented in the treatment of HPV infections.

It is also known that interferons, which are released from infected cells, migrate to uninfected cells and protect them from viral infections [*Atlas, Microbiology, Fundamentals and Applications*, p. 481, MacMillan, New York, London, (1984)]. The activity of interferon on the cell lines of human papilloma virus (especially type 31) as manifested by growth arrest and apoptosis is also reported [Chang et al., *J. Virol.* 76: 8864-8874 (2002)]. Other antimicrobial, antiseptic and or oxygen donating agents, such as carbamide peroxide [Lim et al., *Cytotechnology* 31: 265-270 (1999)] or other germ killing compound generating agents such as hexamethylene tetramine can also help to eradicate viruses.

In an especially preferred embodiment, the inventive composition comprises a combination of lysozyme and one or more therapeutic agents selected from the group consisting of acyclovir, cisplatin vidarabine, uridine, 5-fluorouracil, thiotepa, interferons, podophyllotoxin, trichloroacetic acid, salicylic acid, carbamide peroxide, hexamethylene tetramine, and derivatives thereof, particularly acyclovir and cisplatin.

The inventive composition can be administered, orally, topically or by injection, intramuscular or intravenously. For this purpose, the inventive composition can be formulated in any suitable administration form. In a preferred embodiment, the inventive composition is in the form of tablets, capsules, lozenges, creams, lotions, powders, gels, or sprayable or injectable solutions. In one especially preferred embodiment, the inventive composition is in the form of a tablet, capsule or lozenge. In another especially preferred embodiment, the inventive composition is in the form of a solution. In another especially preferred embodiment, the inventive composition is in the form of a topical cream or lotion.

What is an "effective amount" of the various ingredients needs to be determined empirically depending on the end use and the mode of administration. In this regard, the lysozyme content can be varied over a wide range, preferably from about 0.01 to about 20% by weight of the inventive composition, especially from about 0.1 to about 7% by weight of the inventive composition, particularly from about 0.1 to about 5% by weight of the inventive composition. Additional therapeutic agents, where present, should be used at or below their normal recommended dosages and the entire inventive composition should ordinarily be administered according to the normal dosage regimens of such additional therapeutic agents.

The patient is either a human or an animal. In one preferred embodiment, the patient is a human, especially a woman suffering from or susceptible to cervical cancer. In a particularly preferred embodiment, the inventive formulation is administered to a woman suffering from or susceptible to cervical cancer in the form of an injectable solution. For this particular embodiment, the inventive formulation will be administered to such person typically once or twice daily for a period of days, weeks or months as necessary.

In another embodiment, the patient is a bovine or equine animal, for example, a cow or a horse. In a preferred embodiment, the patient is a cow or a horse, especially one suffering from or susceptible to sarcoids. In a particularly preferred embodiment, the cow or horse is suffering from sarcoids, and the lysozyme is administered to the cow or horse by topically applying a composition comprising the lysozyme to one or more of said sarcoids. In this embodiment, the inventive formulation most preferably comprises the lysozyme in the form of a sprayable solution or a cream or lotion. In this particular embodiment, the inventive formulation will be sprayed onto an area of the animal's skin covering the sarcoids once or twice daily for a period of days, weeks or months as necessary. In another particularly preferred embodiment, the cow or horse is suffering from sarcoids, and the lysozyme is administered to the cow or horse orally, for example, by a tablet or lozenge placed in the animal's mouth, or through the animal's drinking water or feed.

The invention will now be explained in greater detail with reference to the following non-limiting example.

EXAMPLE

A horse having large sarcoid tumors about its body was treated daily by applying copious amounts of a 5% lysozyme solution directly to skin areas covering the tumors. After a period of days, the tumors began to shrink, thereby showing the effectiveness of the lysozyme solution against such tumors.

It should be understood that the preceding detailed description of the invention is merely a detailed description of one preferred embodiment or of a small number of preferred embodiments of the present invention and that numerous changes to the disclosed embodiment(s) can be made in accordance with the disclosure herein without departing from the spirit or scope of the invention. The preceding detailed description of the invention, therefore, is not meant to limit the scope of the invention in any respect. Rather, the scope of the invention is to be determined only by the appended issued claims and their equivalents.

What is claimed is:

1. A pharmaceutical composition for treating a papilloma virus infection in a mammal, said composition comprising (A) an antivirally effective amount of a lysozyme, (B) at least one additional therapeutic agent effective against papilloma virus and (C) a pharmaceutically acceptable carrier.

2. The pharmaceutical composition according to claim 1, wherein the lysozyme is a human recombinant lysozyme.

3. The pharmaceutical composition according to claim 1, wherein the lysozyme is a non-human lysozyme.

4. The pharmaceutical composition according to claim 3, wherein the non-human lysozyme is a hen egg white lysozyme.

5. The pharmaceutical composition according to claim 1, wherein the additional therapeutic agent effective against papilloma virus is acyclovir.

6. The pharmaceutical composition according to claim 1, wherein the additional therapeutic agent effective against papilloma virus is cisplatin.

7. The pharmaceutical composition according to claim 1, which is in the form of a cream, lotion, powder, gel, or sprayable or injectable solution.

8. The pharmaceutical composition according to claim 7, which is in the form of a solution.

9. The pharmaceutical composition according to claim 7, which is in the form of a topical cream or lotion.

10. A method of treating a papilloma virus infection in a patient in need thereof, said method comprising administering to said patient an effective amount therefor of a pharmaceutical composition according to claim 1 for a period of time sufficient to treat said papilloma virus infection.

11. The method according to claim 10, wherein the patient is a human.

12. The method according to claim 11, wherein the human is a woman suffering from or susceptible to cervical cancer.

13. The method according to claim 12, wherein the lysozyme is administered to said woman in the form of tablets, capsules or lozenges.

14. The method according to claim 12, wherein the lysozyme is administered to said woman in the form of an injectable solution.

15. The method according to claim 10, wherein the patient is a bovine animal.

* * * * *